United States Patent [19]

Sawano et al.

[11] Patent Number: 4,515,909
[45] Date of Patent: May 7, 1985

[54] RESINOUS COMPOSITION FOR THE PROLONGED RELEASE OF FRAGRANT SUBSTANCES

[76] Inventors: Kiyohito Sawano, 11-19, Hadeshikogahara, Hiratsuka-shi, Kanagawa-ken; Ryujiro Kouichi, 83-75, Oodonoi, Noda-shi, Chiba-ken; Hideaki Oota, 4-3-3, Takeyama, Midori-ku, Yokohama-shi, Kanagawa-ken; Masashi Takano, 8-15-13, Sugita, Isogo-ku, Yokohama-shi, Kanagawa-ken; Michio Moroe, 2-28-9, Shimorenjaku, Mitaka-shi, Tokyo, all of Japan

[21] Appl. No.: 426,799

[22] Filed: Sep. 29, 1982

[30] Foreign Application Priority Data

Feb. 16, 1982 [JP] Japan .................. 57-23455

[51] Int. Cl.³ .................. A61L 9/01; A61L 9/04
[52] U.S. Cl. .................. 523/102; 424/76; 424/78; 428/905
[58] Field of Search .......... 523/102; 428/905; 424/76, 78

[56] References Cited

U.S. PATENT DOCUMENTS

| | | | |
|---|---|---|---|
| 3,261,746 | 7/1966 | Copley | 167/42 |
| 3,303,046 | 2/1967 | Chebiniak et al. | 117/36.1 |
| 3,688,985 | 9/1972 | Engel | 239/54 |
| 3,725,311 | 4/1973 | Grubb | 252/522 |
| 3,775,227 | 11/1973 | Wilbert et al. | 161/30 |
| 3,876,762 | 4/1975 | Rabussier et al. | 424/78 |
| 3,994,439 | 11/1976 | Van Breen et al. | 239/54 |
| 4,095,031 | 1/1978 | Engle | 526/1 |
| 4,110,261 | 8/1978 | Newland | 252/522 |

FOREIGN PATENT DOCUMENTS

| | | |
|---|---|---|
| 2367087 | 5/1978 | France . |
| 43-6283 | 2/1969 | Japan . |
| 531299 | 8/1971 | Japan . |
| 47-7920 | 3/1972 | Japan . |
| 48-37825 | 11/1973 | Japan . |
| 49-4946 | 2/1974 | Japan . |
| 52-30171 | 3/1975 | Japan . |
| 50-29015 | 9/1975 | Japan . |
| 567423 | 3/1976 | Japan . |
| 5324492 | 8/1976 | Japan . |
| 54-37974 | 1/1979 | Japan . |
| 564270 | 12/1979 | Japan . |
| 56-121560 | 9/1981 | Japan . |
| 1257377 | 12/1971 | United Kingdom . |
| 1538085 | 5/1977 | United Kingdom . |
| 2066665 | 7/1981 | United Kingdom . |

Primary Examiner—Paul Lieberman
Assistant Examiner—Amelia B. Yarbrough
Attorney, Agent, or Firm—Richard M. Barnes

[57] ABSTRACT

A resinous composition for fragrant substances is provided which comprises an ethylene-vinyl acetate copolymer containing from about 5% to about 35% of vinyl acetate monomer, by weight, and a diffusing agent selected from the group consisting of benzyl benzoate, benzyl salicylate, and di-(lower alkyl)phthalates, and mixtures thereof. The diffusing agent is absorbed in the copolymer. When fragrant substances are enclosed in a container made from the resinous composition of the present invention or the composition of the present invention is impregnated with such fragrant substances, a well-balanced, mild fragrance, inherent to the fragrant substance employed, is uniformly released over a long period of time.

13 Claims, 5 Drawing Figures

RESINOUS COMPOSITION FOR THE PROLONGED RELEASE OF FRAGRANT SUBSTANCES

BACKGROUND OF THE INVENTION

The present invention relates to resinous compositions for the prolonged release of fragrant substances. More particularly, the present invention relates to compositions of certain ethylene-vinyl acetate copolymers and one or more specific diffusing agents which, when impregnated with or enclosing a fragrant substance, provide for the uniform release of that fragrant substance over a prolonged period of time.

Fragrant compositions have heretofore been formed into aerosol, gel, liquid, powder and plastic products, of which the water-soluble gel products have found the largest commercial utility. Fragrant compositions, in a water-soluble form, which employ agar, carrageenan, gelatin, or the like as a gelling agent, are prepared by heating such a gelling agent to cause it to melt. A surfactant containing one or more fragrant substances and a dispersion aid such as methanol, ethanol, isopropanol or the like is then added to the molten gelling agent and the resulting composition cooled until it solidifies. One problem with such gel-type fragrant compositions is that the content of the fragrant substances is relatively low, generally, on the order of about 10%.

Therefore, in order to provide for the release of the fragrance over a long period of time, it is necessary to form the fragrant composition into a product of large mass. This, however, results in another problem which is that the evaporation and emission from such a large mass decreases with the passage of time because the volume decreases gradually and the gel surfaces become harder due to evaporation of water. Yet another problem with such gel-type fragrant compositions is that the fragrant substances are unavoidably subjected to heat during preparation, thereby disturbing the balance of the fragrance in the composition and, possibly, causing the fragrant substances to undergo modification.

In order to avoid these problems with water-soluble gel-type fragrant compositions, many improvements have been proposed, including, for example, avoiding the breakage of gel-type fragrant compositions by adding a thermoplastic resin to dibenzilidene or tribenzilidene sorbitol and then solidifying the resulting mixture (Japanese Patent Publication No. SHO 48-37825); obtaining a formed gel product by making use of the steam permeability and porosity of water-containing unsaturated polyester resins (Japanese Patent Publication No. SHO 52-30171); and obtaining a hydrophilic gel by reacting a peptide with a hydrophilic urethane prepolymer (Japanese Patent Publication No. SHO 53-24492).

It is also known to employ one or more fragrant substances adsorbed on silica gel, alumina and the like. One reported improvement on this practice has been to cover each particle of powder or pulverized material, carrying one or more fragrant substances absorbed thereon, with a synthetic resin film, or mixing such powders or pulverized materials in a synthetic resin (Japanese Patent Publication Nos. SHO 43-6283, 56-4270, and 56-7423).

A number of attempts have heretofore been made to impart fragrance to synthetic resins. These attempts have, however, not been particularly successful. In general, there is no miscibility between fragrant substances and synthetic resins and, even if they are mixed together, the resultant mixture loses its effectiveness as a fragrant composition in a short period of time either because the fragrant substance oozes out onto the surface of the synthetic resin or the fragrant substance is hermetically trapped within the interior of the synthetic resin and restrained from diffusing onto the surfaces of the resin, thereby preventing the composition from releasing the fragrant substance.

By way of example, thermoplastic resins of aliphatic hydrocarbons, such as polyethylene, polypropylene and the like, have poor gas permeability while polystyrene-type and polyvinyl acetate-type resins have an extremely high gas permeability. Accordingly, none of these resins are suitably employed as a carrier for fragrant substances.

Among the many proposals that have been made to overcome the aforementioned drawbacks of such synthetic resin-based fragrant products, are employing a hydrophilic polymer of a hydrophilic acrylate or methacrylate carrier for the fragrant substance (Japanese Patent Publication No. SHO 49-4946); employing a chlorine-modified polyethylene or polypropylene coploymer (Japanese Patent Publication No. SHO 50-29015); incorporating a surfactant containing an amine compound as a penetration aid in a synthetic resin (Japanese Patent Publication No. SHO 53-1299); mixing fragrant substances in a polyolefin resin of a lower molecular weight, melting the resulting mixture, forming the molten mixture into pellets, and mixing the resultant pellets in a polyolefin resin of a high molecular weight (Japanese Patent Publication No. SHO 54-37974); and mixing fragrant substances in a copolymer of ethylene and vinyl acetate or ethylene and one of various acrylates (Japanese Patent Laid Open No. SHO 53-98352) and impregnating such copolymers with fragrant substances (Japanese Patent Laid Open No. SHO 56-121560).

The aforementioned proposals have not, however, provided fragrant compositions of any particularly satisfactory commercial value, since they require preparation of special synthetic resins for the specific uses or are limited as to the types of fragrant substances which may be employed.

SUMMARY OF THE INVENTION

A resinous composition for fragrant substances is provided which comprises at least one specific ethylene-vinyl acetate copolymer and a diffusing agent selected from the group consisting of benzyl benzoate, benzyl salicylate and di-(loweralkyl)phthalates and mixtures thereof. The diffusing agent is absorbed in the copolymer. When fragrant substances are enclosed in a container made from the resinous composition of the present invention or the composition of the present invention is impregnated with such fragrant substances, a well-balanced, mild fragrance, inherent to the fragrant substance employed, is released at a constant level over a long period of time.

BRIEF DESCRIPTIONS OF THE DRAWINGS

FIGS. 1 through 5 are diagrams which show, with respect to sample moldings and a control product, the change in the composition of the fragrant formulation after the lapse of a predetermined time period, in comparison to a standard fragrant formulation (LEMON, LIME, HH-7835).

DESCRIPTION OF THE PREFERRED EMBODIMENTS

Figure 1:
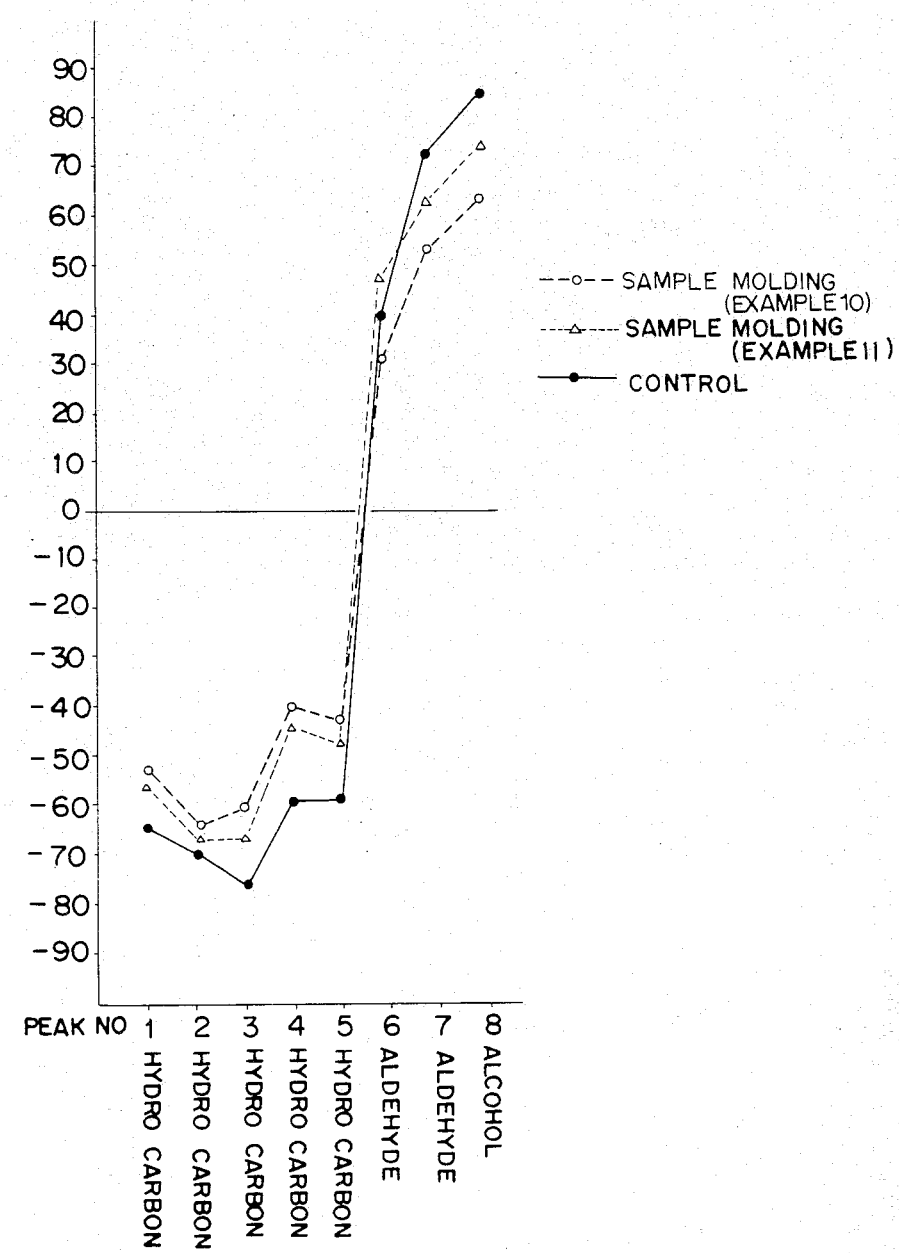

The fragrant compositions of the present invention contain a specific synthetic resin which is an ethylene-vinyl acetate copolymer (hereinafter referred to as "EVA") which contains the vinyl acetate monomer (hereinafter referred to as "VA") in an amount of from about 5% to about 35%, by weight, preferably about 15% to about 30%, by weight.

The second component of the fragrant composition of the present invention is a diffusing agent selected from the group consisting of benzyl benzoate, benzyl salicylate, di-(loweralkyl)phthalates, and mixtures thereof. Preferably, the diffusing agent is selected from the group consisting of benzyl benzoate, benzyl salicylate, dibutylphthalate, diethylphthalate, dimethylphthalate, and mixtures thereof. The total amount of the diffusing agent present in the resinous composition of the present invention may vary depending on the amount of the vinyl acetate monomer present in the EVA, the type of fragrant substance to be employed with the fragrant composition, and its intended application. It is generally preferred to add the diffusing agent in an amount of from about 1% to about 10% by weight of the EVA. The total amount of diffusing agents present will generally increase in proportion to the content of VA in the copolymer.

When the fragrant substance to be employed consists principally of two or more lower esters, ethers, or terpenic hydrocarbons such as limonene, it is preferred to use a lesser amount of the diffusing agent. On the other hand, when the fragrant substance employed consists principally of two or more alcohols, aldehydes, phenols, ketones or higher esters, it is preferred to use a larger amount of the diffusing agent.

The fragrant substances which may be employed with the resinous composition of the present invention include terpenic hydrocarbons, esters, ethers, alcohols, aldehydes, phenols, and ketones. Among the preferred fragrant substances are nonyl alcohol, benzyl alcohol, linalool, undecylenic aldehyde, benzaldehyde, citral, ionone, menthone, amyl acetate, linalyl acetate, dibenzyl ether, eugenol, D-limonene, δ-decalactone and mixtures thereof. When the resinous composition of the present invention is impregnated with the fragrant substance, the fragrant substance will preferably be present in the resinous composition in an amount within the range of from about 1 to about 40% by weight of the composition. A particularly preferred amount is about 20 to about 30% by weight.

The resinous compositions of the present invention are typically prepared by adding the diffusing agent to EVA pellets in a rotary mixer and mixing the two components until the diffusing agent is absorbed by the pellets. The time required for absorption may be substantially decreased by mildly heating during mixing. By way of example, for EVAs containing 28%, 19% and 16% VA, respectively, the preferred temperature ranges during mixing are from about 50° C. to about 60° C., about 60° C. to about 70° C., and about 70° C. to about 76°, respectively. The completion of the absorption of the diffusing agents by the EVA pellets can be determined visually by observing that no diffusing agent is present on the EVA surface. Typically, the absorption step takes from about 1 to about 5 hours, but may be complete in about 1 to about 3 hours.

The resinous composition of the present invention may be prepared in pellet form and then impregnated with one or more fragrant substances. These impregnanted pellets may then be molded into various shapes using techniques known to those skilled in the art and used as room air fresheners and the like. Alternatively, the resinous composition may be molded into containers having an internal void and any desired shape which may be filled with one or more fragrant substances and the container sealed. In this embodiment, a large volume of fragrant substance may be provided which is absorbed by the walls of the container, diffuses through the walls and is released into the surrounding environment.

Suitable colorants, pigments or the like may be incorporated in the resinous composition. Containers molded from the resinous compositions of the present invention may be clear, if so desired, and the fragrant substances contained therein may be colored or not. Additionally, a germicide may be combined with the fragrant substance.

EXAMPLES

The following examples present illustrative but non-limiting embodiments of the present invention. Comparative examples are also provided.

EXAMPLE 1

100 grams of benzyl benzoate were combined with 1 kg of YUKALON EVA X-502 (a product of Mitsubishi Petro Chemical Company Ltd., having a vinyl acetate monomer content of 28% by weight) in a rotary mixer and mixed at a temperature maintained within the range of 50° C. to 60° C. Absorption was visually determined to be complete after about two hours.

EXAMPLE 2

50 grams of benzyl benzoate were combined with 1 kg. of YUKALON EVA V-401 Pellets (a product of Mitsubishi Petro Chemical Company Ltd., having a vinyl acetate monomer content of 19%) in a rotary mixer and mixed at a temperature maintained within the range of from 60° C. to 70° C. Absorption was complete in about 1.5 hours.

EXAMPLE 3

30 grams of benzyl salicylate were combined with 1 kg. YUKALON EVA EVA-41H pellets (a product of Mitsubishi Petro Chemical Company Ltd., having a vinyl acetate monomer content of 16%) in a rotary mixer and mixed at a temperature maintained within the range of from 70° C. to 76° C. Absorption was complete within about 2 hours.

EXAMPLES 4–12

In Examples 4 through 12 set forth below in Table 1, nine exemplary resinous compositions of the present invention were prepared from EVA pellets and various diffusing agents according to the procedure set forth in Examples 1 through 3.

TABLE 1

| Ex. No. | Diffusing Agent | Grams | Resin (1 Kg) | Absorption Temp. (°C.) | Absorption Time (hrs.) |
|---|---|---|---|---|---|
| 4 | Benzyl benzoate | 35 | YUKALON-EVA X-502 | 50-55 | 3.5 |
|   | Dimethyl phthalate | 10 |  |  |  |
| 5 | Benzyl benzoate | 60 | YUKALON-EVA X-502 | 50-60 | 1.5 |
|   | Dibutyl phthalate | 20 |  |  |  |
| 6 | Benzyl salicylate | 25 | YUKALON-EVA EVA-41H | 70-73 | 3.0 |
|   | Diethyl phthalate | 5 |  |  |  |
| 7 | Benzyl benzoate | 90 | YUKALON-EVA V-401 | 60-65 | 4.0 |
|   | Dimethyl phthalate | 5 |  |  |  |
|   | Dibutyl phthalate | 5 |  |  |  |
| 8 | Dibutyl phthalate | 100 | YUKALON-EVA X-502 | 50-55 | 2.0 |
| 9 | Dibutyl phthalate | 30 | YUKALON-EVA EVA-41H | 70-76 | 2.0 |
| 10 | Benzyl benzoate | 30 | YUKALON-EVA EVA-41H | 70-73 | 2.5 |
| 11 | Benzyl benzoate | 20 | YUKALON-EVA EVA-41H | 70-73 | 2.5 |
|    | Dibutyl phthalate | 10 |  |  |  |
| 12 | Benzyl benzoate | 60 | YUKALON-EVA V-401 | 60-63 | 3.0 |
|    | Dimethyl phthalate | 20 |  |  |  |

EXAMPLE 13

TABLE 2[1]

| Fragrant Substance | Resin | Evaporation and Emission Rate (%) | | | | | | |
|---|---|---|---|---|---|---|---|---|
|  |  | 1 day | 2 days | 3 days | 1 week | 2 weeks | 3 weeks | 4 weeks |
| Nonyl alcohol | EVA (VA 28%)[2] | 20 | 40 | 60 | 80 | 80 | 80 | — |
|  | EVA (VA 28%) + BB 10% | 47.5 | 50 | 62.5 | 87.5 | 100 | — | — |
| Benzyl alcohol | EVA (VA 28%)[2] | 23.5 | 41 | 47 | 59 | 64.5 | 68 | — |
|  | EVA (VA 28%) + DBP 7% | 12.5 | 33.5 | 46 | 62.5 | 71 | 76 | — |
| Linalool | EVA (VA 28%)[2] | 54 | 67 | 79 | 93 | 100 | — | — |
|  | EVA (VA 28%) + BB 10% | 49 | 58 | 77 | 89 | 92 | 95 | 100 |
| Undecylenic aldehyde | EVA (VA 28%)[2] | 22.5 | 26 | — | 59.5 | 74 | 78 | 81.5 |
|  | EVA (VA 28%) + BB 10% | 19 | 19.5 | — | 58 | 77 | 80.5 | 85 |
| Benzaldehyde | EVA (VA 28%)[2] | 38 | 51 | 56.5 | 64 | 69.5 | 73 | — |
|  | EVA (VA 28%) + BS 10% | 30 | 40.5 | 50 | 62.5 | 67 | 70 | — |
| Citral | EVA (VA 28%)[2] | 16.5 | 29 | 37.5 | 62.5 | 78 | 86.5 | — |
|  | EVA (VA 28%) + DEP 7% | 11 | 25 | 28 | 55.5 | 69 | 77 | — |
| Ionone | EVA (VA 28%)[2] | 8.5 | 8.5 | 15 | 33.5 | 39 | 42 | — |
|  | EVA (VA 28%) + DMP 7% | 5 | 10 | 14.5 | 38 | 47.5 | 57 | — |
| Menthone | EVA (VA 28%)[2] | 40.5 | 63.5 | 73 | 95.5 | 100 | — | — |
|  | EVA (VA 28%) + DBP 7% | 32.5 | 58.5 | 70.5 | 90 | 96 | 100 | — |
| Amyl acetate | EVA (VA 28%)[2] | 88 | 92 | 100 | — | — | — | — |
|  | EVA (VA 28%) + BB 10% | 80 | 84 | 96 | 100 | — | — | — |
| Linalyl | EVA (VA 28%)[2] | 30.5 | 43.5 | 52 | 74 | 87 | 94.5 | — |
|  | EVA (VA 28%) + DMP 7% | 20.5 | 35.5 | 47 | 73.5 | 83 | 89 | — |
| Dibenzyl ether | EVA (VA 28%)[2] | 0 | 0 | 0 | 5 | 8 | 11.5 | — |
|  | EVA (VA 28%) + DMP 7% | 3 | 3 | 5 | 8.5 | 15.5 | 22 | — |
| Eugenol | EVA (VA 28%)[2] | 0 | 3 | 4.5 | 12.5 | 21 | 30 | — |
|  | EVA (VA 28%) + BS 10% | 3 | 5 | 8.5 | 19.5 | 28.5 | 41.5 | — |
| D-Limonene | EVA (VA 19%)[2] | 68 | 78.5 | 89.5 | 96.5 | 96.5 | 96.5 | — |
|  | EVA (VA 19%) + BB 3% | 64 | 72 | 84 | 92 | 92 | 92 | — |
| δ-Decalactone | EVA (VA 28%)[2] | 0 | 0 | 0 | 10 | 21 | 25 | — |
|  | EVA (VA 28%) + BS 10% | 8.5 | 8.5 | 10 | 25 | 36 | 41.5 | — |

[1]EVA + BB 10% means EVA, which contains 28% of VA, impregnated with 10% benzyl benzoate. "BS 10%" denotes "impregnated with 10% of benzyl salicylate". "DBP 7%", "DEP 7%" and "DMP 7%" mean, respectively, "impregnated with 7% of dibutyl phthalate", "7% of diethyl phthalate" and "7% of dimethyl phthalate".
[2]Presented for comparative purposes only; not a resinous composition of the present invention.

The evaporation and emission rate for 14 different fragrant substances absorbed in resinous compositions of the present invention were compared with comparative compositions comprising EVA without a diffusing agent but impregnated with the same fragrant substance. For each fragrant substance, a sheet of the resinous composition of the present invention (1 cm×1.5 cm×0.3 cm) and a sheet of EVA having the same dimensions were impregnated with the specific fragrant substance until each sheet had absorbed 30% by weight of the fragrant substance. The evaporation and emission rate were determined by weighing each sheet immediately after impregnation and then at periods of one day, two days, three days, one week, two weeks, three weeks, and four weeks post impregnation. The test was conducted at room temperature.

It is apparent from the results summarized above in Table 2 that the resinous compositions of the present invention can accelerate the evaporation and emission of fragrant substances as compared to the evaporation and emission rate for impregnated EVA and, at the same time, can suppress the evaporation and emission rate of fragrant substances having a relatively rapid evaporation and emission rate as compared to the evaporation and emission rate for impregnated EVA.

EXAMPLE 14

The rate of absorption for fourteen different fragrant substances by various resinous compositions of the present invention was compared to the rate of absorption of the same fragrant substances by EVA alone. The resin and the resinous composition employed for each comparison were weighed before being contacted with the fragrant substance and then at two hours after contact and four hours after contact and the weight percentage of the fragrant substance absorbed in that period calculated. The results are summarized below in Table 3.

TABLE 3[1]

| Fragrant Substance | Resin | Absorption Rate (wt. %) | |
|---|---|---|---|
| | | 2 hours later | 4 hours later |
| Nonyl alcohol | EVA (VA 28%)[2] | 7 | 10 |
| | EVA (VA 28%) + BB 10% | 9 | 15 |
| Nonyl alcohol | EVA (VA 19%)[2] | 2 | 2 |
| | EVA (VA 19%) + BB 3% | 4 | 6 |
| Amyl acetate | EVA (VA 28%)[2] | 35 | 50 |
| | EVA (VA 28%) + BB 10% | 45 | 60 |
| Amyl acetate | EVA (VA 16%)[2] | 6 | 7 |
| | EVA (VA 16%) + BB 3% | 7 | 9 |
| Linalool | EVA (VA 28%)[2] | 18 | 25 |
| | EVA (VA 28%) + BB 10% | 20 | 30 |
| Linalool | EVA (VA 19%)[2] | 4 | 6 |
| | EVA (VA 19%) + BB 3% | 5 | 8 |
| Benzyl alcohol | EVA (VA 28%)[2] | 5 | 7.5 |
| | EVA (VA 28%) + DBP 7% | 12.3 | 16.4 |
| Undecylenic aldehyde | EVA (VA 28%)[2] | 16 | 26 |
| | EVA (VA 28%) + DBP 7% | 21.3 | 34.6 |
| Benzaldehyde | EVA (VA 28%)[2] | 13.8 | 25 |
| | EVA (VA 28%) + DMP 7% | 17.8 | 33.3 |
| Citral | EVA (VA 28%)[2] | 6.1 | 11.1 |
| | EVA (VA 28%) + DEP 7% | 9.4 | 14.9 |
| Ionone | EVA (VA 28%)[2] | 2.6 | 5.2 |
| | EVA (VA 28%) + DMP 7% | 6.7 | 6.7 |
| Menthone | EVA (VA 28%)[2] | 22.6 | 34.5 |
| | EVA (VA 28%) + DBP 7% | 28.2 | 44.8 |
| Benzyl acetate | EVA (VA 28%)[2] | 8.3 | 11.9 |
| | EVA (VA 28%) + BS 10% | 8.3 | 14.3 |
| Linalyl acetate | EVA (VA 28%)[2] | 6.3 | 10.1 |
| | EVA (VA 28%) + BS 10% | 8.0 | 12.3 |
| Dibenzyl ether | EVA (VA 28%)[2] | 6.2 | 8.7 |
| | EVA (VA 28%) + DMP 7% | 8.4 | 14.4 |
| Eugenol | EVA (VA 28%)[2] | 6.7 | 12.4 |
| | EVA (VA 28%) + DMP 7% | 8.0 | 13.6 |
| δ-Decalactone | EVA (VA 28%)[2] | 2.2 | 3.3 |
| | EVA (VA 28%) + BS 10% | 3.8 | 5.1 |

[1]The abbreviations have the meanings assigned in Table 2.
[2]Presented for comparative purposes only; not a resinous composition of the present invention.

As is readily apparent from the results summarized in Table 3, the resinous compositions of the present invention exhibit a faster absorption rate as compared to EVA. This increase in absorption rate is advantageous from a commercial standpoint since it permits a faster rate of production. Also, for the embodiment of the present invention in which a container is made of the resinous composition and then filled with a fragrant substance, the greater absorption rate insures that as the fragrant substance is emitted and evaporates from the outer surface of the container, the absorption of the fragrant substance into the resinous composition will occur at a rate sufficient to maintain the external rate of evaporation.

EXAMPLE 15

1 kg. of the resinous composition prepared in Example 1 was combined with 100 grams of a fragrant formulation, FRAGRANT OLIVE HH-6619 (a product of Takasago Perfumery Company, Ltd., Japan, and containing 54% alcohol, 11% esters, 10% aldehydes, 20% hydrocarbons, and 5% other substances) in a rotary mixer and mixed while being maintained at a temperature within the range of from about 50° C. to about 60° C. until the fragrant substance was absorbed in the resinous composition, resulting in fragrant pellets having a fragrance of fragrant olive.

EXAMPLE 16

1 kg. of the resinous composition prepared in Example 2 was combined with 100 grams of a fragrant formulation, LEMON HH-7008 (a product of Takasago Perfumery Company Ltd., Japan, containing 10% alcohol, 32% esters, 27% aldehydes, 23% hydrocarbons such as limonene, and 8% other substances) in a rotary mixer and mixed at a temperature maintained within the range of 50° C. to 60° C. until the fragrant substance was absorbed in the resinous composition, resulting in fragrant pellets having a fragrance of lemon.

EXAMPLE 17

Fragrant pellets having a fragrance of gardenia were prepared by combining 1 kg. of the resinous composition prepared in Example 3 with 100 grams of a fragrant formulation, GARDENIA HH-6944 (a product of Takasago Perfumery Company Ltd., Japan, containing 15% alcohol, 50% esters, 17% aldehydes, 7% hydrocarbons and 11% other substances) in a rotary mixer and mixing these components at a temperature maintained within the range of from 50° C. to 60° C. until the fragrant substance was absorbed in the resinous composition.

EXAMPLE 18

The fragrant pellets prepared in Example 17 were directly injection-molded to form petal-shaped broaches.

EXAMPLE 19

10 mgs. of the resinous composition prepared in Example 1 were charged into a blow-molding machine and heated to a temperature within the range of from 130° C. to 150° C. at which the resinous composition became molten. The molten resinous composition was then extruded into cylindrical molds to continuously produce cylindrical blow-molded products each of which had a wall thickness of 0.5 mm., a diameter of 2 cm., a height of 5 cm., and which were closed at each end except for an opening 2 mm. in diameter at one end. 10 grams of the fragrant formulation, FRAGRANT OLIVE HH-6619, were injected into each cylinder through the opening and then the opening hermetically sealed, by heating, to obtain an air freshener.

The air fresheners were placed in a constant-temperature room maintained at a temperature within the range of from 20° C. to 25° C., for 28 days. The fragrant substances smoothly and steadily evaporated and were emitted from the air fresheners during this time period and, at the end of 28 days, 80% of the fragrant formulation remained in the air fresheners. No substantial difference was noted in the fragrance between the beginning of the test and the end of the test and no leakage of the formulation was observed on the surface of the container.

As a comparative example, cylinders identical in size and shape were injection-molded using YUKLAON EVA X-502 and were each injected with 10 grams of the same fragrant formulation and then hermetically sealed as above (these cylinders are hereinafter referred to as the "control product").

The control product was also placed in a constant-temperature room maintained at a temperature of from 20° C. to 25° C. for 28 days. However, unlike the air fresheners prepared from the resinous composition of the present invention, 92% of the fragrant formulation remained in the control product at the end of the test, thus evidencing the comparatively poor evaporation and emission properties of EVA alone. Subjectively, the fragrance emitted by the control product was noted to have a tendency to lose its balance.

EXAMPLE 20

In order to compare the evaporation and emission of fragrant substances by a resinous composition of the present invention with that of EVA alone. The resin employed was YUKALON EVA EVA-41H (hereinafter referred to as the "control resin"). Bottle-shaped moldings (hereinafter referred to as the "moldings") were fabricated from the control resin by a blow-molding technique to have the dimensions noted in Table 4.

TABLE 4

| Outer diameter: | about 22.4 mm |
| --- | --- |
| Overall height: | about 43 mm |
| Height to the shoulder: | about 27.5 mm |
| Bottom wall thickness: | 1.1–1.2 mm |
| Side wall thickness: | 0.6–0.7 mm |

The resinous composition of the present invention was prepared by maintaining a diffusing agent at a desired temperature and then dipping the blow-molded bottles therein to absorb the diffusing agent. Where two or more different diffusing agents were employed, they were mixed in predetermined proportions prior to dipping the molding therein.

Fragrant articles were prepared by injecting fragrant substances into bottles made of the control resin (hereinafter referred to as "the control product") and into bottles made of the resinous composition of the present invention (hereinafter referred to as the "sample molding").

As the fragrant formulation, LEMON LIME HH-7835 (a product of Takasago Perfumery Company, Ltd., Japan, containing 11% alcohols, 3% esters, 22% aldehydes, 56% hydrocarbons and 7% other substances) was employed. 7 grams of the fragrant formulation were injected into each bottle through the upper-most end and the resulting opening was then hermetically sealed by heating. The injected fragrant formulation filled the bottle to a height of about 2.4 cm., leaving a 17 $cm^2$ evaporation and emission area, exclusive of the bottom area.

The injected sample moldings and control products were weighed and placed on the floor of a constant-temperature room maintained at 23° C. to 28° C. After two weeks, they were again weighed to determine the amount of the fragrant formulation lost through evaporation and emission. At the same time, they were also subjected to sensory evaluation, by a panel of experts, in comparison with a standard fragrant formulation (hereinafter referred to as the "standard fragrant formulation") comprising LEMON LIME HH-7835 which had been stored in a cool and dark place. The comparison was done using standard sniff paper. The fragrant formulation in the sample moldings and control products (hereinafter referred to as the "sample fragrant formulations") were drawn from the upper-most end of the bottles by injectors and then absorbed on standard sniff paper.

The results of the emissions test and the sensory evaluation are summarized below in Tables 5 and 6.

TABLE 5

|  | Weight of Molding (g) | Evaporated and emitted amount after two weeks at 23°–28° C. |
| --- | --- | --- |
| Control product (comparative) | 9.02 | 3.31 g (47.3%) |
| Sample molding (Ex. 10) | 9.00 | 3.21 g (45.9%) |
| Sample molding (Ex. 11) | 9.00 | 3.57 g (51.0%) |

TABLE 6

| Molding | Sensory Evaluation |
| --- | --- |
| Control product: (comparative) | Compared with the standard fragrant formulation, its top note was very weak and freshness had been lost. |
| Sample molding: (Example 10) | Compared with the standard fragrant formulation, no substantial change was recognized with respect to its fragrant tone and it maintained fresh fragrance. |
| Sample molding: (Example 11) | Compared with the standard fragrant formulation, its top note had been slightly weakened but its overall fragrance was kept fresh. |

The sample fragrant formulations were then subjected to a composition analysis employing a gas chromatograph to determine whether the fragrant substances had been uniformly evaporated and emitted.

The analysis procedure is summarized as follows:
(1) The standard fragrant formulation was subjected to a gas chromatographic analysis under the same conditions as the sample fragrant formulations;
(2) Eight principal components corresponding to the main peaks on a gas chromatogram were numbered 1 through 8, respectively, and are summarized in FIG. 1;
(3) The peak area of each of these eight components for the standard fragrant formulation were compared with the peak area of the same component for the sample fragrant formulation which had been in the constant-temperature room for two weeks. The difference between the respective peaks was expressed as a percentage with either a plus symbol (+) or a minus symbol (−);

(4) The analytical results are diagrammatically shown in FIG. 1.

The diagram indicates that the composition balance of the fragrant formulation is more constant as its curve approaches the standard line; that is, the 0-line, and is less wavy.

As shown in FIG. 1, the comparison between the control products and the sample moldings (one sample molding employed the resinous composition of Example 10 and the other the resinous composition of Example 11) indicates that the evaporation and emission rate increases for a fragrant substance as the peak number decreases. As the evaporation and emission rate of the fragrant substance decreases, the peak number increases.

EXAMPLE 21

Bottles indentical in dimension to those prepared in Example 20 were prepared by the same blow-molding technique and then treated to give sample moldings and control products. The control resin employed was YUKALON EVA V-401 and YUKALON EVA EVA-41H. The bottles were injected with 7 grams of the fragrant formulation, WHITE ROSE HH-7833 (a product of Takasago Perfumery Company, Ltd., Japan, containing 45% alcohol, 34% esters, 2% aldehydes, 11% hydrocarbons and 8% other substances). The fragrant formulation was injected to a height of about 2.2 cm. in each molding leaving 15.5 cm$^2$ (exclusive of the bottom area) as the evaporating and emitting area. The moldings were weighed and then placed on the floor of a constant-temperature room, maintained at a temperature of from 23° C. to 28° C., for six weeks and then reweighed and the amount of fragrant formulation evaporated and emitted determined. At the same time, the moldings were subjected to a sensory evaluation carried out in the same manner as in Example 20. The results are summarized below in Tables 7 and 8.

TABLE 7

| | Weight of Molding (g) | Evaporated and emitted amount after six weeks at 23°–28° C. |
|---|---|---|
| Control product (comparative) | 9.19 | 3.26 g (46.6%) |
| Sample molding (Ex. 12) | 9.36 | 2.33 g (33.3%) |
| Control product (comparative) | 9.03 | 2.11 g (30.2%) |
| Sample molding (Ex. 9) | 9.19 | 2.36 g (33.8%) |

TABLE 8

| Molding | Sensory Evaluation |
|---|---|
| Control product: (comparative) | Compared with the standard fragrant formulation, its top note was considerably off-balanced and its overall fragrance strength was weak. |
| Sample molding: (Example 12) | Compared with the standard fragrant formulation, its top note had been slightly weakened but its overall fragrance strength was sufficiently high. No significant difference was found in comparison with the standard fragrant formulation. |
| Control product: (comparative) | Compared with the standard fragrant formulation, its top note was somewhat off-balanced. It was not felt to be fresh as a whole. |

TABLE 8-continued

| Molding | Sensory Evaluation |
|---|---|
| Sample molding: (Example 9) | Compared with the standard fragrant formulation, no significant difference was observed with respect to its top note. It was well-balanced as a whole and no significant difference was found compared with the standard fragrant formulation. |

Figure 2:
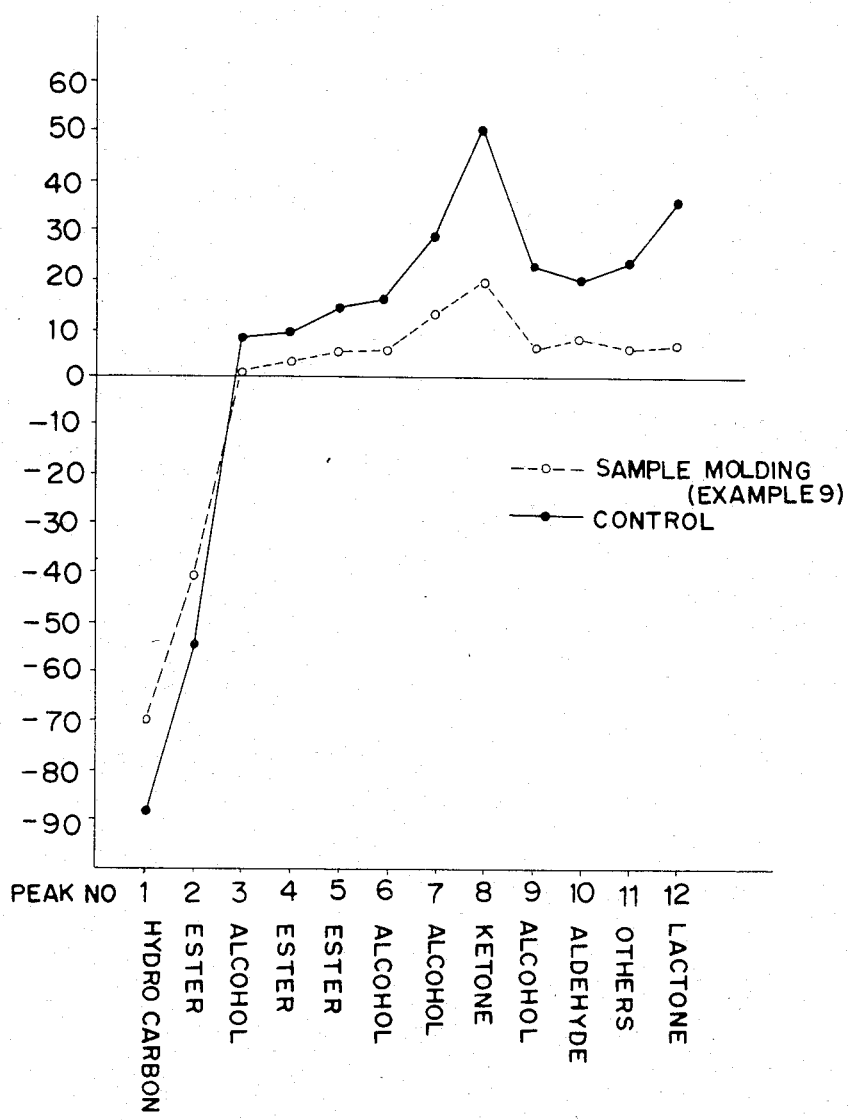
Figure 3:
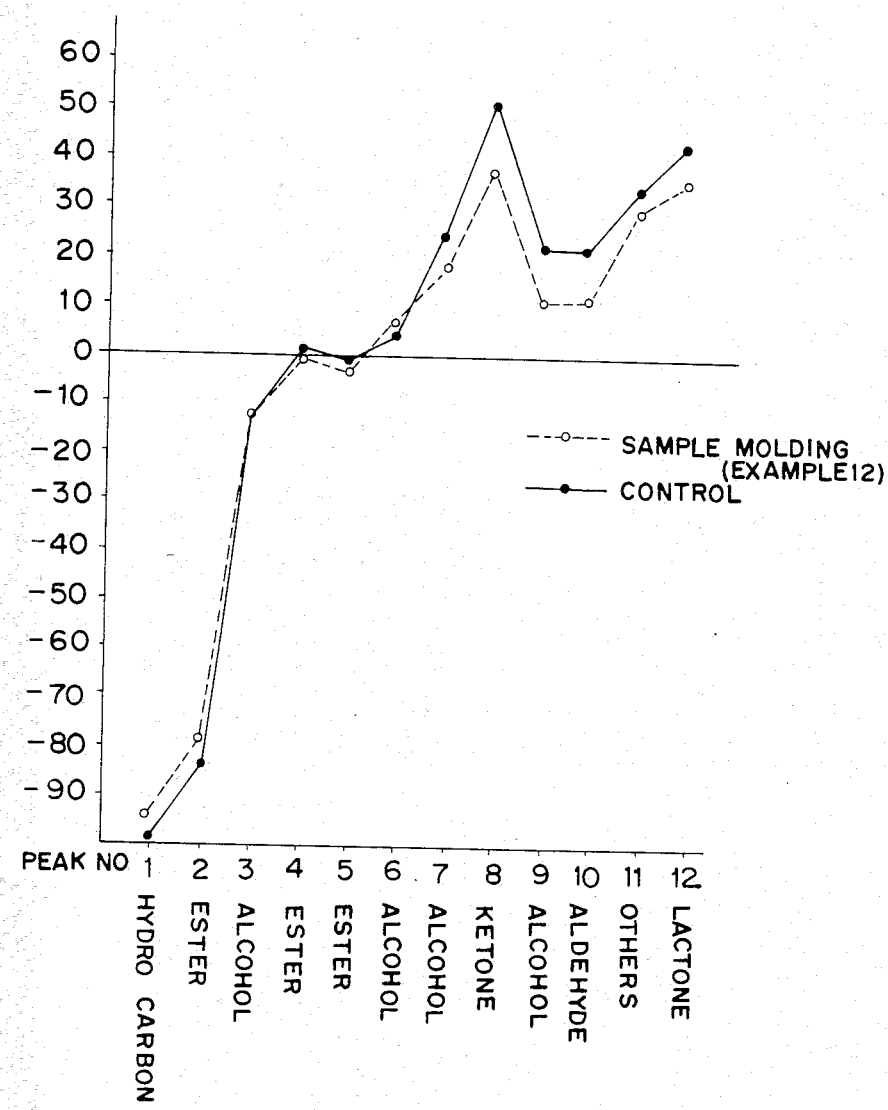

These sample fragrant formulations were then subjected to gas chromatographic analysis as set forth in Example 20. Twelve principal fragrant components were identified and their peaks assigned numbers 1 through 12, respectively. The results are shown in FIG. 2 and FIG. 3 and show that fragrant articles manufactured from the resinous compositions of the present invention are effective in maintaining fragrance balance.

EXAMPLE 22

Bottles having the dimensions set forth in Example 20 were fabricated by the blow-molding technique and then treated as set forth in Example 20 to give sample moldings and control products. YUKALON EVA VA-401 and YUKALON EVA EVA-41H were employed as the control resin.

As the fragrant formulations, JASMINE HH-7834 (a product of Takasago Perfumery Company, Ltd., Japan, containing 15% alcohols, 41% esters, 22% aldehydes, 3% hydrocarbons, and 19% other substances) was employed. 7 grams of this fragrant formulation were injected into each of the bottles to a height of about 2 cm. leaving 14 cm$^2$ (exclusive of the bottom area) as the evaporating and emitting area. The bottles were weighed and placed on the floor of a constant-temperature room, maintained at 23° C. to 28° C., for six weeks and then reweighed and the amount of the fragrant formulation evaporated and emitted calculated. At the same time, they were also subjected to a sensory evaluation, by a panel of experts, which was conducted as set forth in Example 20. The results are summarized below in Tables 9 and 10.

TABLE 9

| | Weight of Molding (g) | Evaporated and emitted amount after six weeks at 23°–28° C. |
|---|---|---|
| Control product (comparative) | 9.14 | 1.75 g (25.1%) |
| Sample molding (Ex. 7) | 9.40 | 1.70 g (24.4%) |
| Control product (comparative) | 9.07 | 1.10 g (15.7%) |
| Sample molding (Ex. 6) | 9.32 | 1.64 g (23.5%) |

TABLE 10

| Molding | Sensory Evaluation |
|---|---|
| Control product: (comparative) | Compared with the standard fragrant formulation, its fragrance strength had been weakened significantly as a whole. It was insufficient in freshness. |
| Sample molding: (Example 7) | Compared with the standard fragrant formulation, its fragrance strength was somewhat weaker as a whole. However, its fragrance balance was well maintained. |
| Control product: (comparative) | Compared with the standard fragrant formulation, its top note was somewhat off-balanced. As a whole, its fragrance strength was felt to be insufficient. |
| Sample molding: (Example 6) | Compared with the standard fragrant formulation, its top note had been slightly weakened but its overall fragrance balance had been |

| Molding | Sensory Evaluation |
|---|---|
| | well maintained and the fragrant formulation had a long-lasting characteristic. |

Figure 4:
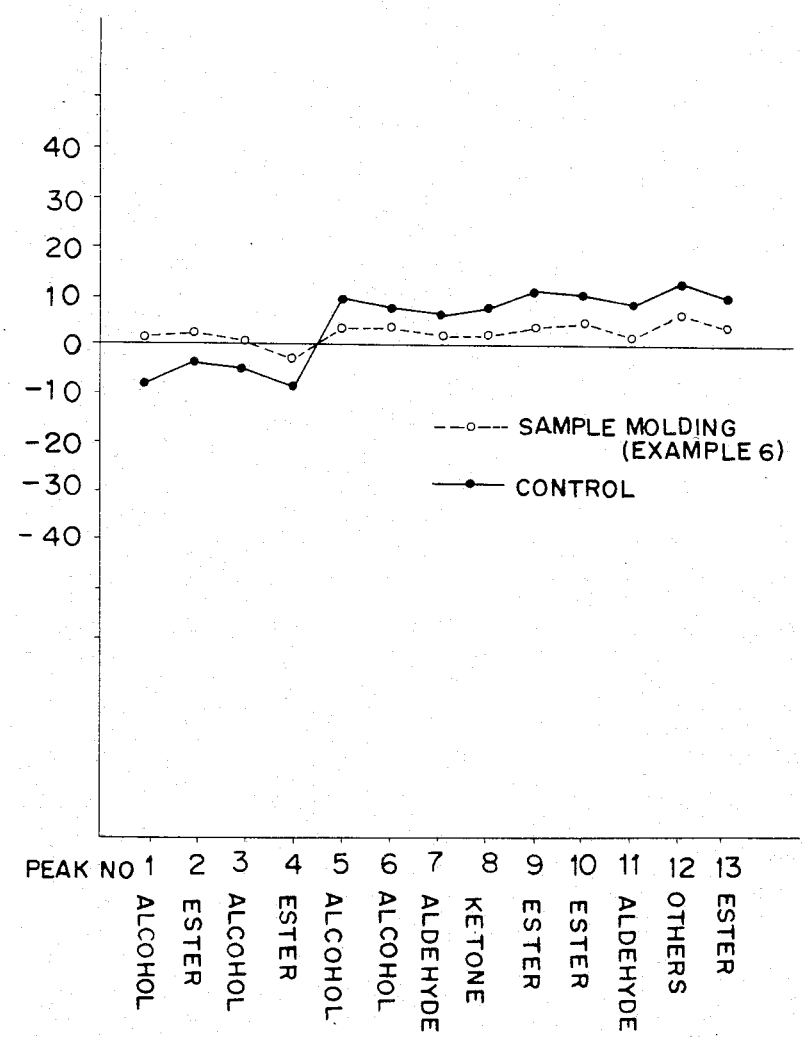
Figure 5:
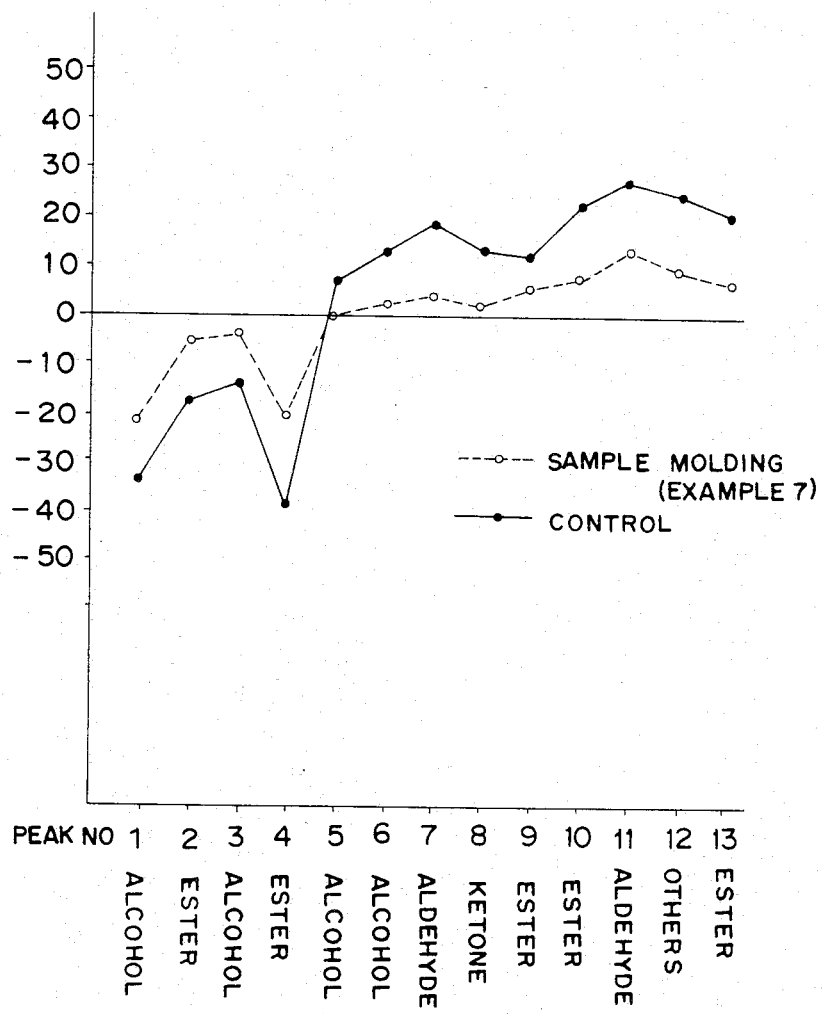

The sample fragrant formulations were then subjected to gas chromatographic analysis as described in Example 20 and thirteen principal fragrant components were identified and their peaks assigned numbers 1 through 13, respectively. The results are shown in FIG. 4 and FIG. 5.

It is clear from these evaluations that fragrant articles manufactured from resinous compositions of the present invention effectively maintain the fragrance balance.

We claim:

1. A fragrant article, comprising an ethylene-vinyl acetate copolymer impregnated with a diffusing agent and a fragrant substance, said copolymer comprising from about 15% to about 30% of vinyl acetate monomer, by weight, and about 85% to about 70% of ethylene monomer, by weight, said diffusing agent being selected from the group consisting of benzyl benzoate, benzyl salicylate, and mixtures thereof, and being absorbed in the copolymer in an amount of from about 1% to about 10% by weight of the copolymer.

2. The fragrant article of claim 1 wherein the fragrant substance is selected from the group consisting of terpenic hydrocarbons, esters, ethers, alcohols, aldehydes, phenols, ketones, and mixtures thereof.

3. The fragrant article of claim 2 wherein the fragrant substance is selected from the group consisting of nonyl alcohol, benzyl alcohol, linalool, undecylenic aldehyde, benzaldehyde, citral, ionone, menthone, amyl acetate, linalyl acetate, dibenzyl ether, eugenol, D-limonene, δ-decalactone, and mixtures thereof.

4. A fragrant article, comprising an hermetically sealed container enclosing a fragrant substance, said container comprising an ethylene-vinyl acetate copolymer impregnated with a diffusing agent, said copolymer comprising from about 15% to about 30% of vinyl acetate monomer, by weight, and about 85% to about 70% of ethylene monomer, by weight, said diffusing agent being selected from the group consisting of benzyl benzoate, benzyl salicylate, and mixtures thereof.

5. The fragrant article of claim 4 wherein the fragrant substance is selected from the group consisting of terpenic hydrocarbons, esters, ethers, alcohols, aldehydes, phenols, ketones, and mixtures thereof.

6. The fragrant article of claim 2 wherein the fragrant substance is selected from the group consisting of nonyl alcohol, benzyl alcohol, linalool, undecylenic aldehyde, benzaldehyde, citral, ionone, menthone, amyl acetate, linalyl acetate, dibenzyl ether, eugenol, D-limonene, δ-decalactone, and mixtures thereof.

7. A method of making the fragrant article of claim 1, comprising mixing the copolymer and the diffusing agent at a temperature within the range of from about 50° C. to about 76° C. until the diffusing agent is completely absorbed by the copolymer, and then contacting the impregnated copolymer with the fragrant substance at ambient temperature until the fragrant substance is absorbed by the impregnated copolymer.

8. The method of claim 7 wherein the copolymer is mixed with the diffusing agent for about from 1 to about 5 hours.

9. A fragrant article, consisting essentially of an ethylene-vinyl acetate copolymer impregnated with a diffusing agent and a fragrant substance, said copolymer consisting essentially of from about 15% to about 30% of vinyl acetate monomer, by weight, and about 85% to about 70% of ethylene monomer, by weight, said diffusing agent consisting essentially of from about 1% to about 10%, by weight of the copolymer, of a compound selected from the group consisting of benzyl benzoate, benzyl salicylate, and mixtures thereof.

10. The fragrant article of claim 9 wherein the article comprises a sealed container enclosing the fragrant substance, the container comprising the impregnated copolymer.

11. The fragrant article of claim 9 wherein the fragrant substance is selected from the group consisting of terpenic esters, ethers, alcohols, aldehydes, phenols, ketones, and mixtures thereof.

12. A method of making the fragrant article of claim 4, comprising mixing the copolymer and the diffusing agent at a temperature within the range of from about 50° C. to about 76° C. until the diffusing agent is absorbed by the copolymer in an amount of from about 1% to about 10% by weight of the copolymer, molding the resulting impregnated copolymer into a container having an internal void, and filling the void with a fragrant substance.

13. A method of making the fragrant article of claim 1, comprising mixing the copolymer and the diffusing agent at a temperature within the range of from about 50° C. to about 76° C. until the diffusing agent is absorbed by the copolymer in an amount of from about 1% to about 10% by weight of the copolymer, and impregnating the resinous composition with a fragrant substance in an amount of from about 1% to about 40% by weight of the fragrant article.

* * * * *

UNITED STATES PATENT AND TRADEMARK OFFICE
CERTIFICATE OF CORRECTION

PATENT NO. : 4,515,909

DATED : May 7, 1985

INVENTOR(S) : Sawano et al.

It is certified that error appears in the above-identified patent and that said Letters Patent is hereby corrected as shown below:

Col. 13, Line 50, "claim 2" should be -- claim 5 --

Signed and Sealed this

Fifteenth Day of September, 1987

Attest:

DONALD J. QUIGG

*Attesting Officer*     *Commissioner of Patents and Trademarks*